US012616784B2

(12) United States Patent
Gao et al.

(10) Patent No.: US 12,616,784 B2
(45) Date of Patent: May 5, 2026

(54) ONLINE DRY POWDER A-AND-DRY POWDER B DISPENSING DEVICE FOR BLOOD PURIFICATION

(71) Applicant: SWS HEMODIALYSIS CARE CO., LTD., Chongqing (CN)

(72) Inventors: Guangyong Gao, Chongqing (CN); Guikang Ye, Chongqing (CN); Jin Tong, Chongqing (CN); Mingzhong Lai, Chongqing (CN); Junquan Zhou, Chongqing (CN); Yuan Liu, Chongqing (CN)

(73) Assignee: SWS HEMODIALYSIS CARE CO., LTD., Chongqing (CN)

( * ) Notice: Subject to any disclaimer, the term of this patent is extended or adjusted under 35 U.S.C. 154(b) by 370 days.

(21) Appl. No.: 18/565,151

(22) PCT Filed: Jun. 16, 2022

(86) PCT No.: PCT/CN2022/099045
§ 371 (c)(1),
(2) Date: Nov. 29, 2023

(87) PCT Pub. No.: WO2023/142338
PCT Pub. Date: Aug. 3, 2023

(65) Prior Publication Data
US 2024/0277908 A1     Aug. 22, 2024

(30) Foreign Application Priority Data
Jan. 26, 2022     (CN) .......................... 202210092011.1

(51) Int. Cl.
*A61M 1/16*         (2006.01)
*B65D 83/06*        (2006.01)

(52) U.S. Cl.
CPC ........ *A61M 1/1656* (2013.01); *A61M 1/1666* (2014.02); *B65D 83/06* (2013.01)

(58) Field of Classification Search
CPC .... A61M 1/1656; A61M 1/1666; B65D 83/06
See application file for complete search history.

(56) References Cited

U.S. PATENT DOCUMENTS 4,812,239 A     3/1989   Mills et al.
5,762,769 A *   6/1998   Gotsu ..................... G01N 27/06
                                                              436/63

FOREIGN PATENT DOCUMENTS

CN       104117105 A     10/2014
CN       206228664 U      6/2017
(Continued)

*Primary Examiner* — Ariana Zimbouski
(74) *Attorney, Agent, or Firm* — NKL Law; Allen Xue

(57)     ABSTRACT

An online dry powder A-and-dry powder B dispensing device for blood purification has a casing, two connecting slide blocks movably connected in the casing. A machine interface is respectively provided on the connecting slide blocks and a preparation interface is respectively provided on two opposite faces of the two connecting slide blocks. A connector is detachably connected to the casing. A dry powder container A and a dry powder container B are respectively in communication with the connector via a pipeline. The dry powder A and the dry powder B are simultaneously or separately connected to a hemodialysis machine for online preparation of concentrated solutions. When a dry powder mechanism is removed, the cleaning and disinfection function of the machine is available for cleaning and disinfecting channels and the interfaces in the dispensing mechanism.

9 Claims, 5 Drawing Sheets

(56)         References Cited

FOREIGN PATENT DOCUMENTS

| CN | 208927217 U |   | 6/2019 |
|----|-------------|---|--------|
| CN | 210303201 U | * | 4/2020 |
| CN | 114470376 A |   | 5/2022 |
| JP | 3937421 B2  | * | 6/2007 |

* cited by examiner

ONLINE DRY POWDER A-AND-DRY POWDER B DISPENSING DEVICE FOR BLOOD PURIFICATION

TECHNICAL FIELD

The present invention relates to the technical field of medical instruments, in particular to an online dry powder A-and-dry powder B dispensing device for blood purification.

BACKGROUND

Dialysis treatment needs to be performed with dialysate, which is a fluid for solute exchange with blood on either side of a dialysis membrane during hemodialysis. A plurality of substances contained in the dialysate would react chemically to produce precipitation (mostly calcium carbonate), so they are usually divided into a component A and a component B before being prepared into the dialysate, to be specific, they are divided into a concentrated solution A and a concentrated solution B, which are separately sucked into a dialysis machine and mixed with reverse osmosis water to prepare the dialysate immediately before any treatment; The concentrated solution B is slightly alkaline according to pH value and prone to growing bacteria. The bacterial growth is effectively inhibited when the concentrated solution B is prepared in dry powder. In addition, to facilitate transportation and storage, the component A and the component B are normally made into dry powder, namely, dry powder A and dry powder B, and the reverse osmosis water is added to prepare the concentrated solutions immediately before use. The preparation processes of the dialysate are formulated as follows: dialysate=(concentrated solution A+reverse osmosis water)+(concentrated solution B+reverse osmosis water), concentrated solution A=dry powder A+reverse osmosis water, and concentrated solution B=dry powder B+reverse osmosis water.

There are two ways for dialysate dispensing: one is to prepare the concentrated solution A and the concentrated solution B separately and then use them in the dialysis machine, and the other is to prepare the concentrated solution A separately and prepare the concentrated solution B online with the dry powder B. There is no device that prepares the concentrated solution A and the concentrated solution B online with the dry powder A and the dry powder B synchronously.

SUMMARY

To overcome the shortcomings of the prior art, the present invention provides an online dry powder A-and-dry powder B dispensing device for blood purification. In order to achieve the above-mentioned objective, the present invention provides the following solutions:

An online dry powder A-and-dry powder B dispensing device for blood purification, which includes a casing, wherein two connecting slide blocks are movably connected in the casing, the two connecting slide blocks are oppositely disposed, a machine interface is respectively provided on the connecting slide blocks, a preparation interface is respectively provided on two opposite faces of the two connecting slide blocks, and the preparation interfaces on the two connecting slide blocks communicate with each other when the flip cover is closed;

further includes a connector detachably connected to the casing, wherein the connector is located between the two connecting slide blocks, one side, facing the two connecting slide blocks, of the connector is respectively provided with a consumable interface, and the consumable interface matches the position of the preparation interface on the corresponding side;

further includes a dry powder container A and a dry powder container B, wherein the dry powder container A and the dry powder container B are respectively in communication with the connector via a pipeline.

According to the above-mentioned solution, the dry powder A and the dry powder B are simultaneously or separately connected to a hemodialysis machine for online dialysate preparation. When the dialysate is prepared online, the connector is connected to the casing. In that case, the preparation interface is in communication with the consumable interface on the corresponding side, and the machine interface on the connecting slide block is communicated with the machine, so that the preparation mechanism is in communication with a dry powder mechanism to form a preparation passage; the reverse osmosis water in the machine enters the dry powder container A and the dry powder container B sequentially or separately after passing through the machine interface, the connecting slide block, the preparation interface, the consumable interface and the connector in order; and the concentrated solutions prepared in the dry powder container A and the dry powder container B enter the machine in the reverse direction of that of the reverse osmosis water, thus realizing simultaneously or separately online preparation of the concentrated solutions in the dry powder container A and the dry powder container B. Before cleaning and disinfection, the connector is disassembled from the casing, the two connecting slide blocks are moved towards each other and compressed together. In that case, the preparation interfaces on the two connecting slide blocks are in communication with one another to form a closed loop of the preparation mechanism interfaces. As a result, the cleaning and disinfection function of the machine is available for cleaning and disinfecting channels and the interfaces in the dispensing mechanism.

Preferably, a flip cover is rotatably connected to an upper end of the casing, the flip cover is connected to a push block by means of a push mechanism, and the push block is connected to the connecting slide block at the corresponding position by means of a first linkage for pushing the connecting slide block at the corresponding position to move.

With this arrangement, when cleaning and disinfection are required, the push mechanism and the push block are driven to move by turning the flip cover, and then the push block pushes the connecting slide block at the corresponding position to move.

Preferably, a return spring is provided between the push block and the connecting slide block at the corresponding positions.

Preferably, the push mechanism includes a push rod and two second linkages, wherein one end of the push rod is hinged to the flip cover, and the other end thereof is hinged to the two second linkages; one end of one second linkage is hinged to the push rod, and the other end thereof is hinged to the casing; and one end of the other second linkage is hinged to the push rod, and the other end thereof is hinged to the push block.

With this arrangement, when the flip cover is turned, the push rod pushes the two second linkages to rotate synchronously, and during the rotation of the two second linkages, the push block is pushed to move forward until transverse self-locking is achieved when the two second linkages are collinear. In addition, the second linkages and the push rod are arranged in this way to save effort.

Preferably, a locking mechanism is further included, wherein the locking mechanism includes a rotary shaft rotatably provided on the flip cover, a fixture block, a shifting block and a torsional spring are provided on the rotary shaft; one end of the torsional spring is compressed on the shifting block, and the other end thereof is compressed on the flip cover; and a groove is provided in the casing to engage with the fixture block.

With this arrangement, when the flip cover is turned down, the fixture block will be automatically fit into the groove in the casing and locked under the action of the torsional spring, so as to lock on the cleaning and disinfection state. To release the lock, the shifting block is toggled to drive the rotary shaft to rotate until the fixture block disengages from the groove.

Preferably, a guide groove is respectively provided in the two opposite faces of the two connecting slide blocks in the vertical direction, and the side, facing the two connecting slide blocks, of the connector is respectively provided with a guide rib to engage with the guide groove.

With this arrangement, during the mounting process of the dry powder mechanism, the preparation interface of the connecting slide block is automatically aligned with and compressed on the consumable interface on the connector by means of the engagement of the guide groove and the guide rib, so as to realize the communication and sealing of a channel.

Preferably, two machine interfaces and two preparation interfaces are disposed on each of the connecting slide blocks, one in and one out respectively; and two consumable interfaces are disposed on the side, facing the two connecting slide blocks, of the connector, one in and one out, respectively.

Preferably, an open groove is provided in the casing and the connector is fit into the open groove.

Preferably, the casing is also provided with a guide mechanism, and the push block is in sliding engagement with the guide mechanism.

With this arrangement, when the two connecting slide blocks slide to the middle, the interfaces on the connecting slide blocks will be automatically aligned and compressed as limited by the guide mechanism, avoiding offset during the movement.

Compared with the prior art, the present invention has the following beneficial effects: according to an aspect of the present invention, the dry powder A and the dry powder B are simultaneously or separately connected to a hemodialysis machine for online preparation of the concentrated solution A and the concentrated solution B; and according to a further aspect of the present invention, when the dry powder mechanism is removed, the cleaning and disinfection function of the machine is available for cleaning and disinfecting the channels and the interfaces in the dispensing mechanism, so that the preparation process of the dialysate is greatly facilitated, and the overall structure is simple and easy to use.

DETAILED DESCRIPTION OF THE PREFERRED EMBODIMENTS

Figure 1:
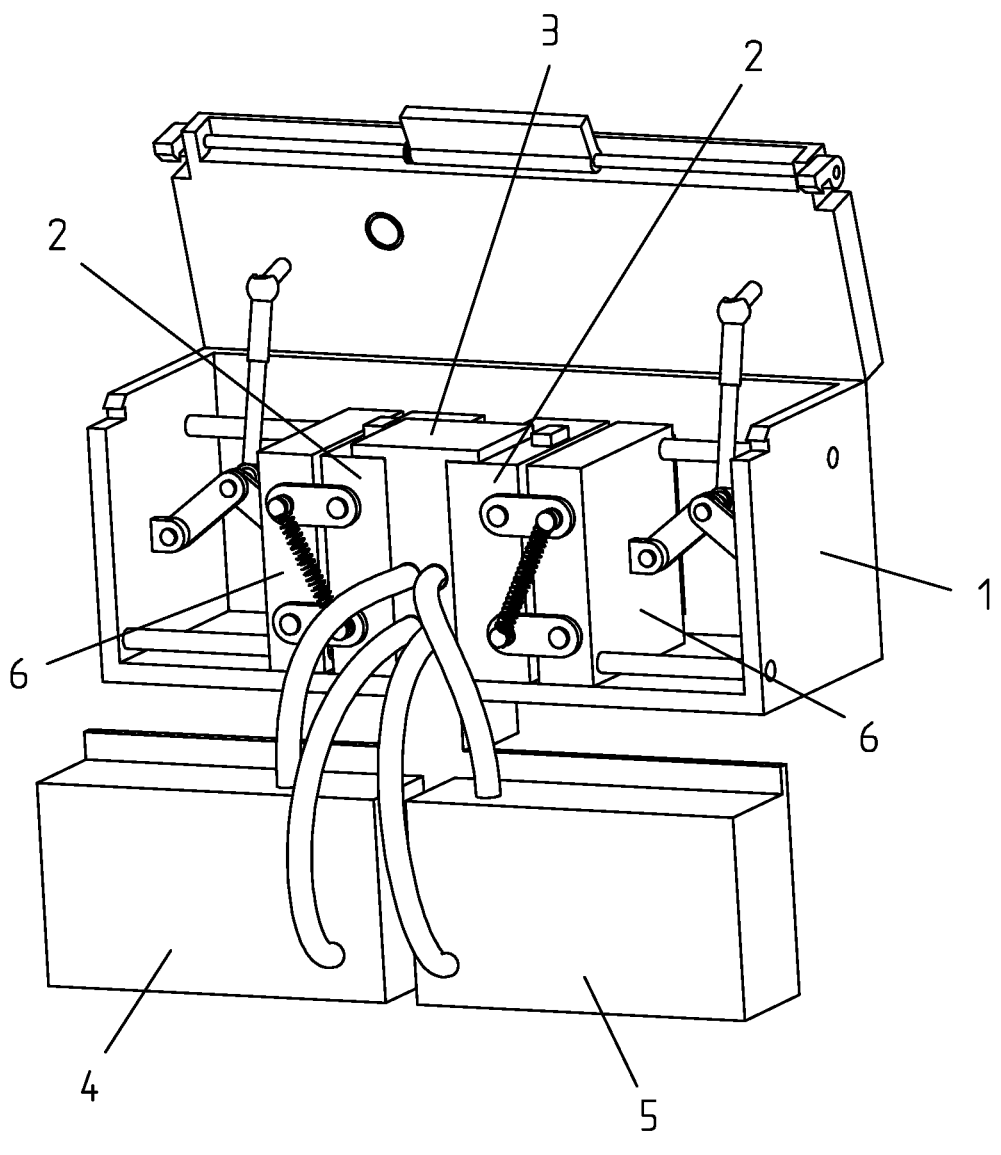
FIG. 1 is a structural diagram of the present invention.

The present invention will be described in further detail with reference to experimental examples and preferred embodiments. However, the following examples should not be construed as limit to the scope of above subjects of the present invention, and technologies realized based on the contents of the present invention shall be incorporated in the scope of the present invention.

In the description of the present invention, it should be noted that, the direction or position relations indicated by the terms "longitudinal", "transverse", "upper", "lower", "front", "rear", "left", "right", "vertical", "horizontal", "top", "bottom", "inner", "outer" and so forth are the direction or position relations based on the drawings, only to facilitate description of the present invention and simplified description, but not to indicate or imply that the indicated device or element must have a special direction, be made or operated in a special direction, thus it cannot be construed as the restriction to the present invention.

In the description of the present invention, the terms "mounting", "connected with" and "connection" shall be understood in a broad sense unless otherwise specified and defined clearly, for example, mechanical connection or electrical connection, or internal communication between two elements; and directly connected, or indirectly connected through a medium. For those of ordinary skill in the art, the specific implications of the above terms in the present invention can be comprehended in accordance with specific conditions.

As shown in FIG. 1 to FIG. 5, an online dry powder A-and-dry powder B dispensing device for blood purification, which includes a preparation mechanism and a dry powder mechanism detachably connected to the preparation mechanism. The preparation mechanism includes a casing 1, a flip cover 11 is rotatably connected to an upper end of the casing 1, a front end of the casing 1 is designed with an open or a notch, two connecting slide blocks 2 are movably connected in the casing 1, the two connecting slide blocks 2 are oppositely disposed, and the open or notched design of the front end of the casing 1 facilitates the mounting of the dry powder mechanism.

The flip cover 11 is connected to a push block 6 by means of a push mechanism, wherein two sets of the push mechanisms and the push blocks 6 are respectively disposed to push the connecting slide blocks 2 at the corresponding positions to move. Alternatively, one set of the push mechanism is designed to push the two connecting slide blocks to move at the same time. The push block 6 is connected to the connecting slide block 2 at the corresponding position by means of a first linkage 8; one end of the first linkage 8 is rotatably connected to the push block 6, and the other end thereof is rotatably connected to the connecting slide block 2; and two first linkages 8 are disposed on either side of the connecting slide block 2 and the push block 6, respectively. In addition, a return spring 62 is provided between the push block 6 and the connecting slide block 2 at the corresponding positions. The connecting slide block 2 is in a self-locking state when the first linkage 8 rotates to a horizontal position.

The push mechanism is used to push the push block 6 to move when the flip cover 11 is turned. In this embodiment, the push mechanism includes a push rod 71 and two second linkages 72, wherein one end of the push rod 71 is hinged to the flip cover 11, and the other end thereof is hinged to the two second linkages 72; one end of one second linkage 72 is hinged to the push rod 71, and the other end thereof is hinged to the casing 1; and one end of the other second linkage 72 is hinged to the push rod 71, and the other end thereof is hinged to the push block 6. With this arrangement, a leverage labor-saving mechanism is formed between a hinge point of the push rod 71 and the two second linkages and the two second linkages, and less labor is required as the mechanism moves downwards. The push rod 71 may also be disposed in a telescopic structure or an intermittent transmission structure, thereby playing the role of half stroke. That is, partial stroke belongs to idle stroke, during which no force is transmitted to the push block 6, and the flip cover can be turned to the bottom during the turning process.

Alternatively, the push rod is directly connected to the push block without arrangement of the labor-saving mechanism. Specifically, one end of the push rod is hinged to the flip cover and the other end thereof is hinged to the push block.

In order to ensure that the push block moves to correct position in the movement process, a guide mechanism is disposed in the casing 1, and the guide mechanism is in sliding engagement with the push block in the horizontal direction. The guide mechanism is selected from a group consisting of a guide rod, a slide way and a guide groove. In this embodiment, the guide mechanism is a guide rod 61 passing through the push block 6 in a sliding manner, and at least two guide rods 61 are disposed.

The connecting slide block 2 has an internal cavity. A machine interface 21 is disposed on the connecting slide block 2, the machine interface 21 is located at a rear end of the connecting slide block 2, a preparation interface 22 is respectively disposed on two opposite faces of the two connecting slide blocks 2. When the flip cover 11 is closed, the preparation interfaces 22 on the two connecting slide blocks 2 are communicated, and the machine interface 21 and the preparation interface 22 are communicated with the internal cavity of the connecting slide block 2.

The dry powder mechanism includes a connector 3 detachably connected to the casing 1, the connector 3 is located between the two connecting slide blocks 2, and the connector 3 has an internal cavity; a consumable interface 31 is respectively disposed on two faces, facing the two connecting slide blocks 2, of the connector 3; the consumable interface 31 is communicated with the internal cavity of the connector 3; and the consumable interface 31 matches the position of the preparation interface 22 on the corresponding side. That is, when the connector 3 is connected to the dispensing mechanism, the consumable interface 31 on the connector 3 is communicated with the preparation interface 22 on the connecting slide block 2 on the corresponding side.

In this embodiment, an open groove is provided in the casing 1 and the connector 3 is fit into the open groove in service.

A guide groove 23 is respectively provided in the two opposite faces of the two connecting slide blocks 2 in the vertical direction, and the side, facing the two connecting slide blocks 2, of the connector 3 is respectively provided with a guide rib 32 to engage with the guide groove 23. In addition, an upper end of the connector 3 is provided with a protrusion extending outward in the horizontal direction. When the connector 3 is connected to the dispensing mechanism, the protrusion at the upper end of the connector 3 abuts against the upper end of the connecting slide block 2 on the corresponding side. When the connector 3 is pressed down, the connecting slide block 2 is driven to move downwards as the protrusion abuts against the upper end of the connecting slide block 2. In that case, the guide rib 32 is fit into the guide groove 23 and moves up and down along the guide groove, thereby limiting the position and avoiding any offset of the connector or the connecting slide block during the connection process.

In this embodiment, two machine interfaces 21 and two preparation interfaces 22 are disposed on each of the connecting slide blocks 2, one in and one out respectively; and two consumable interfaces 31 are disposed on the side, facing the two connecting slide blocks 2, of the connector 3, one in and one out, respectively.

A dry powder container A 4 and a dry powder container B 5 are further included, wherein the dry powder container A 4 and the dry powder container B 5 are disposed below the connector 3 and in communication with the connector 3 via a pipeline, respectively. Since the connector 3 is in a higher position, when the dry powder mechanism is disassembled, the residual solution in the pipelines will not flow out of the consumable interface 31 and cause contamination.

This embodiment further includes a locking mechanism, wherein the locking mechanism includes a rotary shaft 91 rotatably provided on the flip cover 11, a fixture block 92, a shifting block 93 and a torsional spring 94 are provided on the rotary shaft 91; the rotary shaft passes through the torsional spring 94, one end of the torsional spring 94 is compressed on the shifting block 93, and the other end thereof is compressed on the flip cover 11; and the fixture block 92 is respectively disposed on two ends of the rotary shaft 91, and a groove 12 is provided in the casing 1 to engage with the fixture block 92. A latch bolt is respectively provided on the fixture block and the groove. When the flip cover is pressed down, the two latch bolts of the locking block and the locking groove slide against each other. When they slide in place, the fixture block is locked into the groove under the action of the torsional spring to achieve self-locking. To release the lock, the shifting block is manually toggled to drive the rotary shaft and the fixture block to rotate until the fixture block disengages from the groove. Alternatively, the locking process is manually operated without providing the latch bolt.

Optionally, a position transducer is provided on the flip cover at the position corresponding to the connecting slide block, and the next operation will not be proceeded unless the flip cover is turned in place and a signal is detected by the position transducer, thus improving the operation safety.

Figure 2:
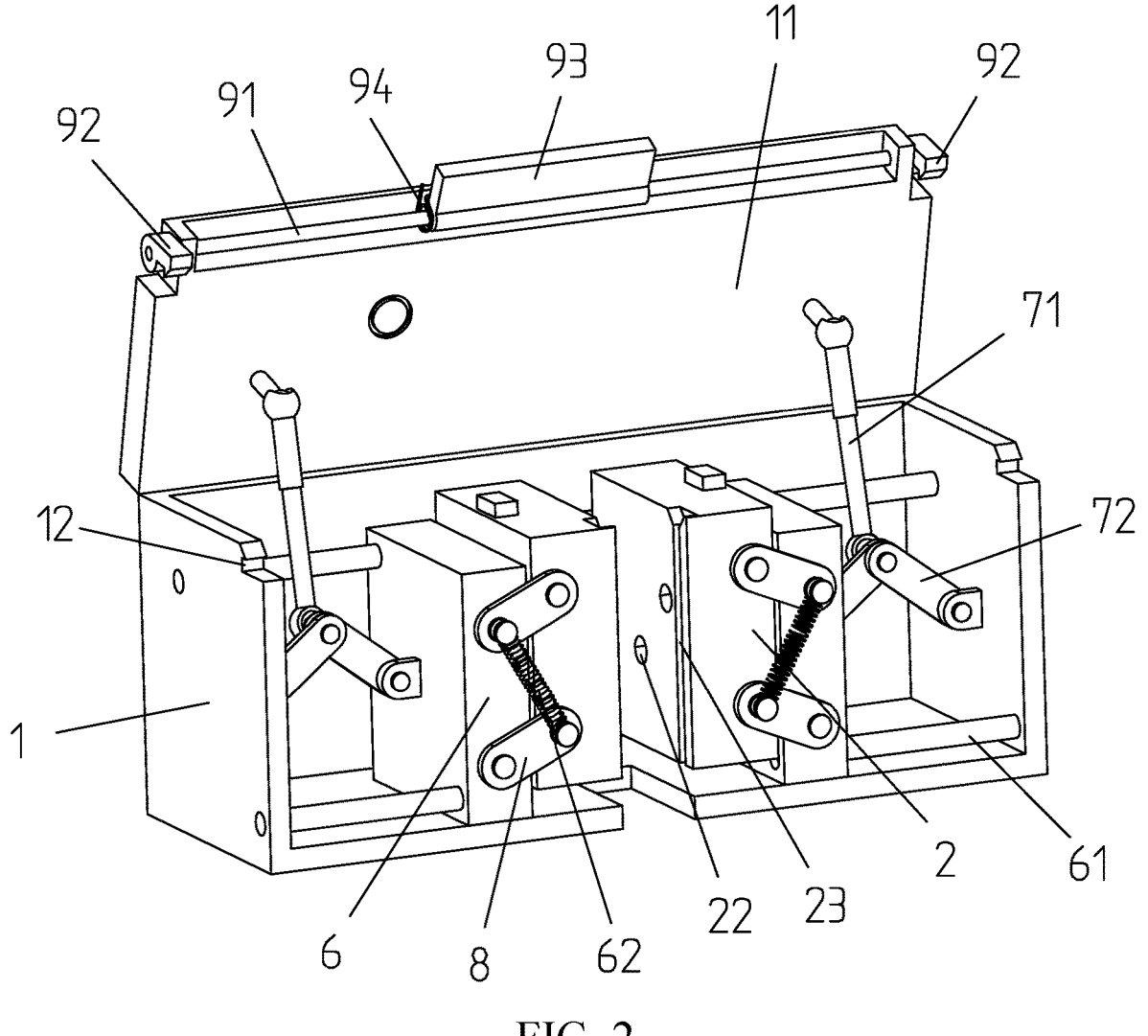
FIG. 2 is a structural diagram of a preparation mechanism of FIG. 1.
Figure 3:
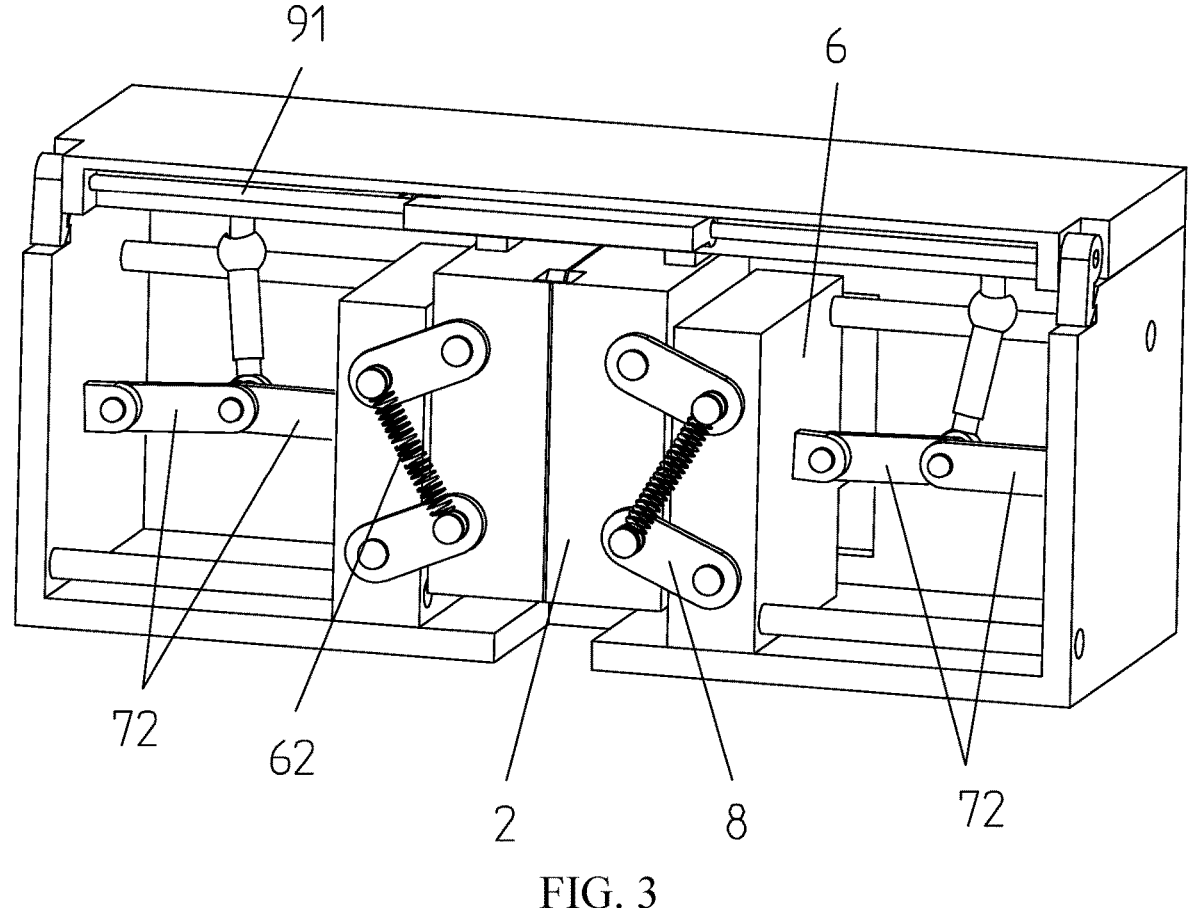
FIG. 3 is a structural diagram of the preparation mechanism of FIG. 1 in the cleaning and disinfection state.
Figure 4:
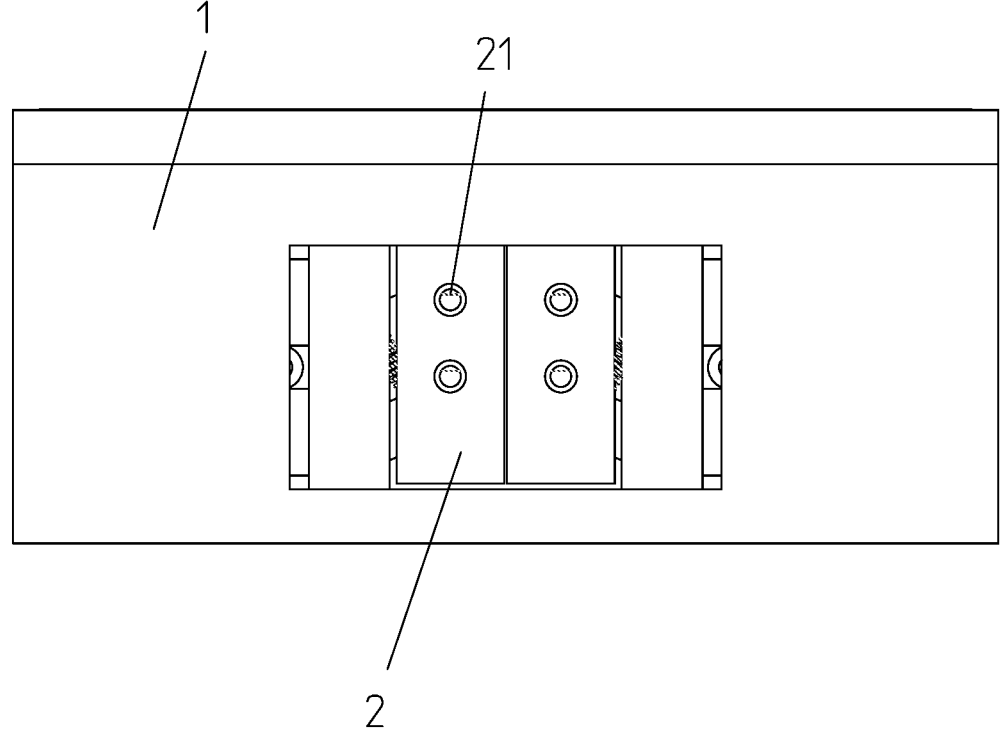
FIG. 4 is a rear view of FIG. 3.
Figure 5:
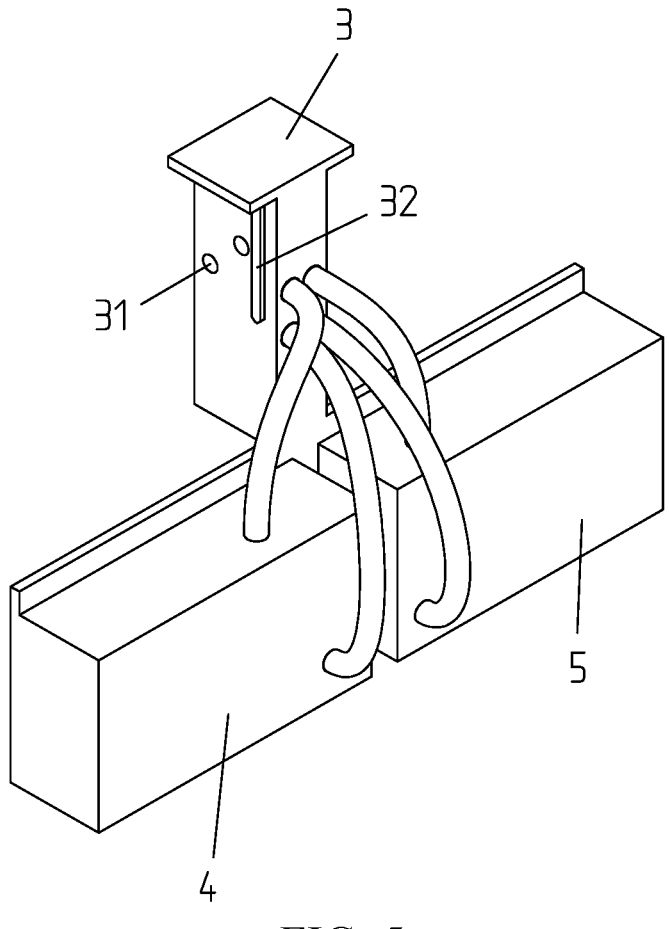
FIG. 5 is a structural diagram of a dry powder mechanism of FIG. 1.

The use process of the present invention is as follows:

When the flip cover 11 is opened, the two connecting slide blocks 2 are separated to two sides under the action of the return spring 62 and switched to a standby state (refer to FIG. 2). After that, the connector 3 is connected to the preparation mechanism (refer to FIG. 1), and the two connecting slide blocks 2 clamp the connector 3 under the action of the first linkage 8. In that case, the preparation interface 22 is in communication with the consumable interface 31 on the corresponding side, and the machine interface 21 on the connecting slide block 2 is communicated with the machine, so that the preparation mechanism is in communication with a dry powder mechanism to form a preparation passage; the reverse osmosis water in the machine enters the dry powder container A and the dry powder container B sequentially or separately after passing through the machine interface 21, the connecting slide block 2, the preparation interface 22, the consumable interface 31 and the connector 3 in order; and the concentrated solutions prepared in the dry powder container A and the dry powder container B enter the machine in the reverse direction of that of the reverse osmosis water, thus realizing simultaneously or separately online preparation of the dialysate in the dry powder container A and the dry powder container B. Before cleaning and disinfection, the connector 3 is disassembled from the casing 1, the flip cover is closed downwards, the two connecting slide blocks 2 are moved towards each other and compressed together under the action of the second linkages and the push blocks by means of the push rods (refer to FIG. 3). When the two connecting slide blocks 2 are compressed together, the preparation interfaces 22 on the two connecting slide blocks 2 are in communication with one another to form a closed loop of the preparation mechanism interfaces for cleaning and disinfection. As a result, the fixture block 92 of the locking mechanism is fit into the groove 12 for locking, so that the cleaning and disinfection function of the machine is available for cleaning and disinfecting channels and the interfaces in the dispensing mechanism. To open the flip cover, the shifting block 93 is toggled upwards and unlocked, and the flip cover is opened.

The foregoing description of the preferred embodiments of the present invention has been presented for the purpose of illustration. It should be understood that those of ordinary skill in the art may make various modifications and changes in accordance with the concept of the present invention without creative work. Therefore, all technical solutions that can be obtained by those skilled in the art through logical analysis, reasoning, or limited experiments on the basis of the concept of the present invention shall be incorporated in the protection scope defined by the claims.

The invention claimed is:

1. An online dry powder A-and-dry powder B dispensing device for blood purification, characterized by comprising a casing (1), wherein two connecting slide blocks (2) are movably connected in the casing (1), the two connecting slide blocks (2) are oppositely disposed, a machine interface (21) is respectively provided on the connecting slide blocks (2), a preparation interface (22) is respectively provided on two opposite faces of the two connecting slide blocks (2), and the preparation interfaces (22) on the two connecting slide blocks (2) correspond in position;

further comprising a connector (3) detachably connected to the casing (1), wherein the connector (3) is located between the two connecting slide blocks (2), one side, facing the two connecting slide blocks (2), of the connector (3) is respectively provided with a consumable interface (31), and the consumable interface (31) matches the position of the preparation interface (22) on the corresponding side; and further comprising a dry powder container A (4) and a dry powder container B (5), wherein the dry powder container A (4) and the dry powder container B (5) are respectively in communication with the connector (3) via a pipeline.

2. The online dry powder A-and-dry powder B dispensing device for blood purification according to claim 1, characterized in that a flip cover (11) is rotatably connected to an upper end of the casing (1), the flip cover (11) is connected to a push block (6) by means of a push mechanism, and the push block (6) is connected to the connecting slide block (2) at the corresponding position by means of a first linkage (8) for pushing the connecting slide block (2) at the corresponding position to move.

3. The online dry powder A-and-dry powder B dispensing device for blood purification according to claim 2, characterized in that a return spring (62) is provided between the push block (6) and the connecting slide block (2) at the corresponding positions.

4. The online dry powder A-and-dry powder B dispensing device for blood purification according to claim 2, characterized in that the push mechanism comprises a push rod (71) and two second linkages (72), wherein one end of the push rod (71) is hinged to the flip cover (11), and the other end thereof is hinged to the two second linkages (72); one end of one second linkage (72) is hinged to the push rod (71), and the other end thereof is hinged to the casing (1); and one end of the other second linkage (72) is hinged to the push rod (71), and the other end thereof is hinged to the push block (6).

5. The online dry powder A-and-dry powder B dispensing device for blood purification according to claim 2, characterized by further comprising a locking mechanism, wherein the locking mechanism comprises a rotary shaft (91) rotatably provided on the flip cover (11), a fixture block (92), a shifting block (93) and a torsional spring (94) are provided on the rotary shaft (91); one end of the torsional spring (94) is compressed on the shifting block (93), and the other end thereof is compressed on the flip cover (11); and a groove (12) is provided in the casing (1) to engage with the fixture block (92).

6. The online dry powder A-and-dry powder B dispensing device for blood purification according to claim 1, characterized in that two machine interfaces (21) and two preparation interfaces (22) are disposed on each of the connecting slide blocks (2), one in and one out respectively; and two consumable interfaces (31) are disposed on the side, facing the two connecting slide blocks (2), of the connector (3), one in and one out, respectively.

7. The online dry powder A-and-dry powder B dispensing device for blood purification according to claim 1, characterized in that an open groove is provided in the casing (1) and the connector (3) is able to be fit into the open groove.

8. The online dry powder A-and-dry powder B dispensing device for blood purification according to claim 2, characterized in that the casing (1) is also provided with a guide mechanism, and the push block (6) is in sliding engagement with the guide mechanism.

9. The online dry powder A-and-dry powder B dispensing device for blood purification according to claim 1, characterized in that a guide groove (23) is respectively provided in the two opposite faces of the two connecting slide blocks (2) in the vertical direction, and the side, facing the two connecting slide blocks (2), of the connector (3) is respectively provided with a guide rib (32) to engage with the guide groove (23).

* * * * *